United States Patent [19]
Gronauer

[11] Patent Number: 5,344,441
[45] Date of Patent: Sep. 6, 1994

[54] ANTENNA ARRANGEMENT WITH SUPPLY CABLE FOR MEDICAL APPLICATIONS

[76] Inventor: Volker Gronauer, Römerbrunnenweg 38, 8832 Weissenburg, Fed. Rep. of Germany

[21] Appl. No.: 127,109

[22] Filed: Sep. 27, 1993

Related U.S. Application Data

[63] Continuation of Ser. No. 908,705, Jul. 2, 1992.

[30] Foreign Application Priority Data

Jul. 3, 1991 [DE] Fed. Rep. of Germany ....... 4122050

[51] Int. Cl.$^5$ ............................................. A61N 5/02
[52] U.S. Cl. .................................. 607/156; 607/102; 606/29; 606/41
[58] Field of Search ................................ 606/27–34, 606/41; 607/100, 101, 154–156

[56] References Cited

U.S. PATENT DOCUMENTS

| | | | |
|---|---|---|---|
| 4,641,649 | 2/1987 | Walinsky et al. | 128/786 |
| 4,643,186 | 2/1987 | Rosen et al. | 128/784 |
| 4,699,157 | 10/1987 | Shonk | 128/784 |
| 4,841,988 | 6/1989 | Fetter et al. | 128/784 |
| 4,998,933 | 3/1991 | Eggers et al. | 606/41 |
| 5,061,267 | 10/1991 | Zeiher | 606/40 |

FOREIGN PATENT DOCUMENTS

| | | |
|---|---|---|
| 034826 | 2/1981 | European Pat. Off. . |
| 105677 | 4/1984 | European Pat. Off. . |
| 139607 | 5/1985 | European Pat. Off. . |
| 248753 | 5/1987 | European Pat. Off. . |
| 372100 | 6/1990 | European Pat. Off. . |
| 2832466 | 7/1978 | Fed. Rep. of Germany . |
| 3743578 | 12/1987 | Fed. Rep. of Germany . |

OTHER PUBLICATIONS

Int. J. Hyperthermia, 1988, vol. 4, No. 6, S. 609–615.
Kunststoff-Taschenbuch, 17, Auflage, Carl Hanser Yerlag, 1967.
Trans. on Microwave Theory and Tech.—vol. 38, No. 1.

Primary Examiner—Stephen C. Pellegrino
Assistant Examiner—M. Peffley
Attorney, Agent, or Firm—Dena Meyer Weker

[57] ABSTRACT

The invention discloses an antenna arrangement with a supply line in the form of a coaxial cable arrangement suitable for high frequencies, in particular for medical applications of heat in hollow parts of the body, an extrusion process for the production thereof, a dilatation catheter with the antenna arrangement and a procedure for a dilatation treatment. The coaxial cable arrangement comprises a continuous inner conductor, an insulator arranged cylindrically around the inner conductor, a shielding device applied around the insulator in a first section of the coaxial cable arrangement which begins at the proximal end of the coaxial cable arrangement, a second section beginning at the distal end of the first section of the coaxial cable arrangement and ending at the distal end of the coaxial cable arrangement, said second section serving as an antenna and being designed without an insulator or a shielding device around the continuous inner conductor. The coaxial cable arrangement furthermore comprises a third section which begins at the proximal end of the antenna arrangement and which is shorter than the first section of the coaxial cable arrangement. The third section of the coaxial cable arrangement is more rigid than the other sections, due to the fact that gaps in the knitted, braided or wrapped material of the shielding device are closed by a filling material.

13 Claims, 4 Drawing Sheets

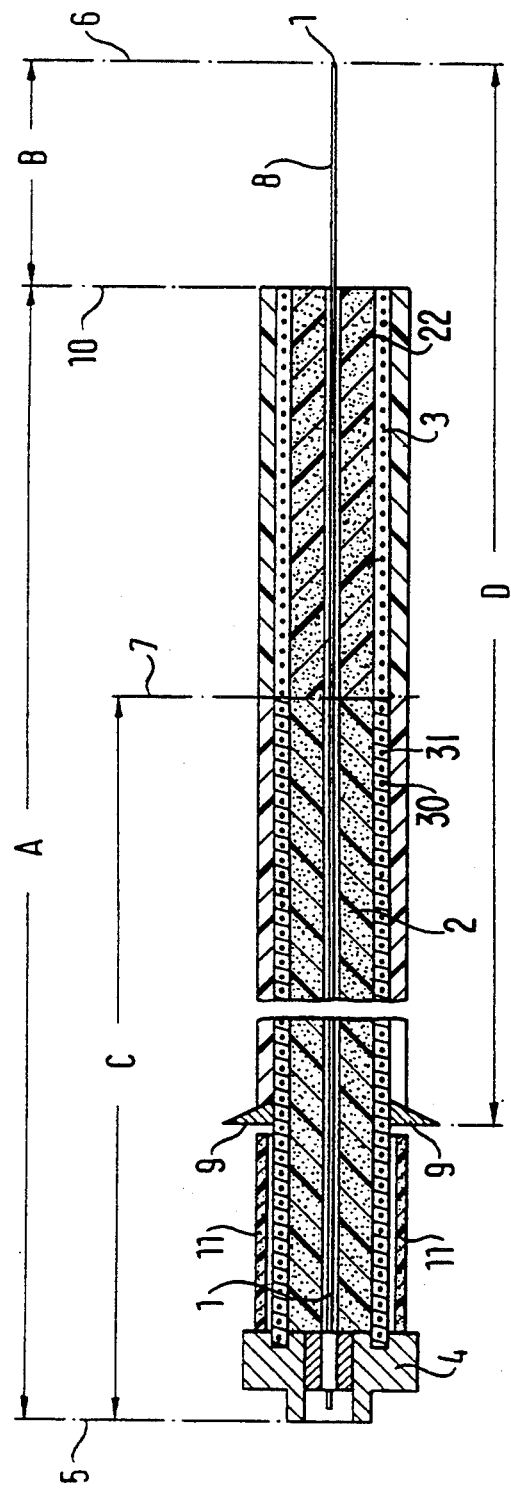
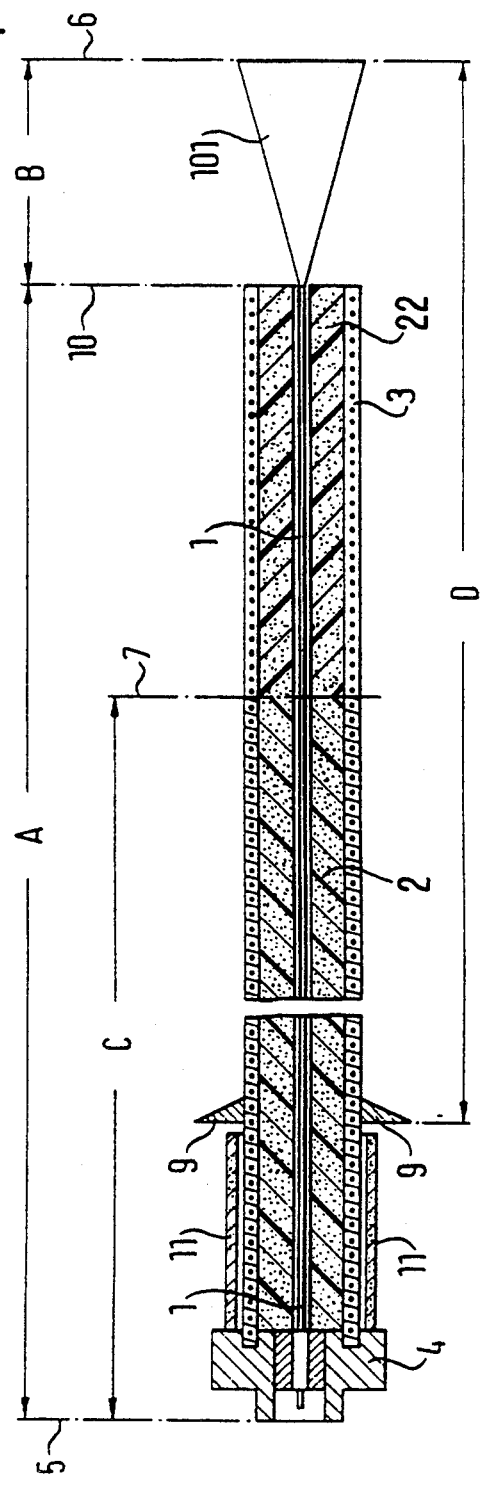

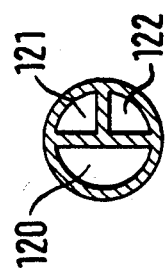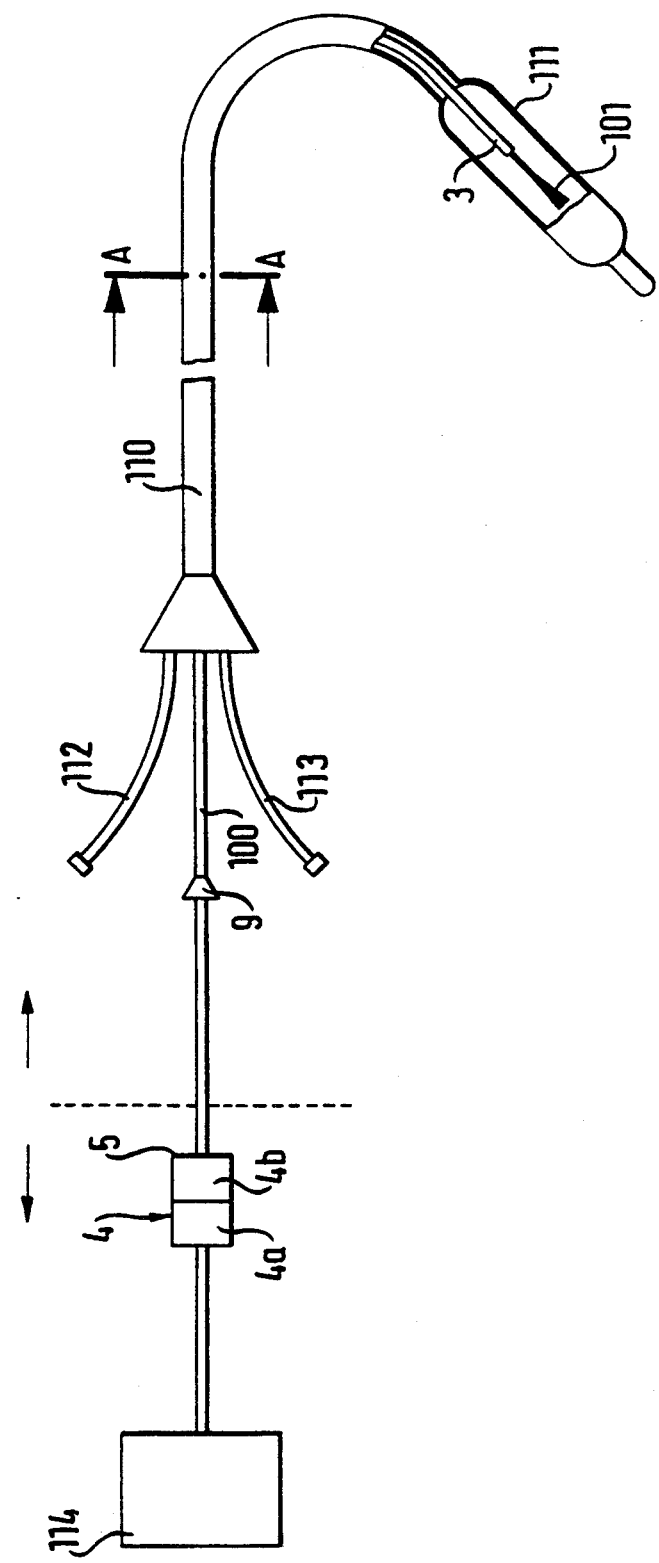

ANTENNA ARRANGEMENT WITH SUPPLY CABLE FOR MEDICAL APPLICATIONS

This application is a continuation, of application Ser. No. 07/908,705 filed Jul. 2, 1992.

FIELD OF THE INVENTION

The invention relates to a rod-shaped antenna arrangement with a supply cable in the form of a coaxial cable assembly suitable for high-frequencies, in particular for medical applications of heat in body cavities. Employment of this cable with special balloon catheters for coronary angioplasty is particularly useful.

BACKGROUND OF THE INVENTION

When blood circulation problems, caused by depositions (atheromateous), such as in pelvic, leg or coronary arteries, leading to stenosis, are cured by widening the arteries or breaking up the depositions, or percutaneous transluminal re-canalization, (dilation), the treatment often causes the artery wall to be injured or dissected as a consequence of the medical treatment, (i.e. iatrogenic injuries). Cutaneous flaps hanging from the blood vessel wall into the vessel obstruct the blood flow and may cause vascular occlusion or, in the case of coronary arteries, a heart attack. There are two obvious alternatives to avoid such complications: A balloon catheter may be used to place "stents" (such as wire meshes) into the vessel in order to mechanically stabilize the vessel wall and keep the vessel open. This process, however, makes the occurence of a thrombosis highly probable. An alternative is stated in volume 38, No. 1, January 1990 of Transactions on Microwave Theory and Techniques: "Percutaneous, transluminal microwave balloon angioplasty" by Rosen A. et al. A "hot balloon", such as a mostly multi-luminous balloon catheter, which is equipped with an asymmetric dipole suitable for radiating electromagnetic microwaves, is inserted and supplied with high-frequency energy by a cable inserted into a lumen. This dilatation catheter is inserted into the vessel in a pressure-free state and without being supplied with high-frequency energy and is then supplied with pressure to achieve the desired widening or blasting effect. Subsequently, high-frequency microwave energy is supplied to the dipole in the catheter so that the vessel wall and the direct vicinity of the catheter balloon are heated to a temperature of more than 50° C for a short period. This causes the protein-substance to coagulate so that cutaneous flaps are bonded to the vessel wall.

The microwave high-frequency energy which serves to heat the tissue must be supplied to an antenna dipole in the balloon catheter with as little energy loss as possible, through the coaxial cable assembly of the dilatation catheter. If the attenuation of the coaxial cable is too high, undesirable heat will be generated in the lumen of the catheter in which the coaxial cable assembly is located. This undesirable generation of heat may cause a dangerous coagulation of the blood surrounding the catheter tube. At the same time, however, the cable assembly must be easy to bend in the distal area, in particular when applied in coronary vessels, so that it can be inserted into the vessel concerned even through narrow bends. In the proximal area a certain minimum rigidity is required to insert the cable assembly into the narrow lumen of a catheter and push it further therein. Furthermore, the diameter of the cable assembly should be as small as possible to minimize the diameter required for the lumen.

For this reason, the coaxial cable assemblies used in dilatation catheters comprise a shield consisting of a flat or round conductor, either wound or braided, and covered by a thin metal tube in the proximal area to enhance the rigidity. A disadvantage of this construction, however, is that the metal tube to be pushed over the cable for the sake of rigidity must be relatively thick so that the effective diameter of the cable becomes too large. This reduces the available room for pushing the cable within the lumen. It may even become necessary to use a catheter tube of a larger diameter. Furthermore, such a cable is complex and expensive to produce and not very efficient because a separate manufacturing step must be included to provide for an adequate connection of the tube to the coaxial cable.

Another approach used for cable assemblies in dilatation catheters is to separately produce two cable sections of different rigidity and electrically and mechanically connect them at a common interface with a microconnector plug. However, this will detract from the electric transmission quality of the cable assembly due to the additional attenuation caused by the interface. Another disadvantage is the complex construction and the high manufacturing costs. In addition, the patient runs the risk of the connection accidentally being severed during the treatment.

There is a need for an improved arrangement with a supply line in the form of a coaxial cable assembly suitable for high-frequency operation for medical applications particularly in hollow organs of the human body.

SUMMARY OF THE INVENTION

The coaxial cable assembly provided comprises a continuous inner conductor, an insulator arranged cylindrically around the inner conductor, a shielding device applied around the insulator in a first section of the coaxial cable arrangement which begins at the proximal end of the coaxial cable arrangement, a second section beginning at the distal end of the first section of the coaxial cable arrangement, this second section serving as an antenna and being designed without an insulator or a shielding around the continuous inner conductor. The coaxial cable arrangement further comprises a third section which begins at the proximal end of the antenna arrangement and which is shorter than the first section of the coaxial cable arrangement. The third section of the coaxial cable arrangement is more rigid than the other sections due to the incorporation of a filling material.

Filling materials include solder and an electrically conductive plastic material.

A process for making the coaxial cable arrangement is also provided.

BRIEF DESCRIPTION OF THE DRAWINGS

FIG. 1 is a cross-section of an embodiment of an antenna arrangement according to the present invention.

FIG. 2 is a cross-section of a second embodiment of an antenna arrangement according to the present invention with a sectional antenna form.

FIG. 5 is an outer view of a dilatation catheter with an antenna arrangement as described in the present invention.

FIG. 6 is a cross-section A—A of the dilatation catheter shown in FIG. 5.

DETAILED DESCRIPTION OF THE PREFERRED EMBODIMENTS

Figure 3:
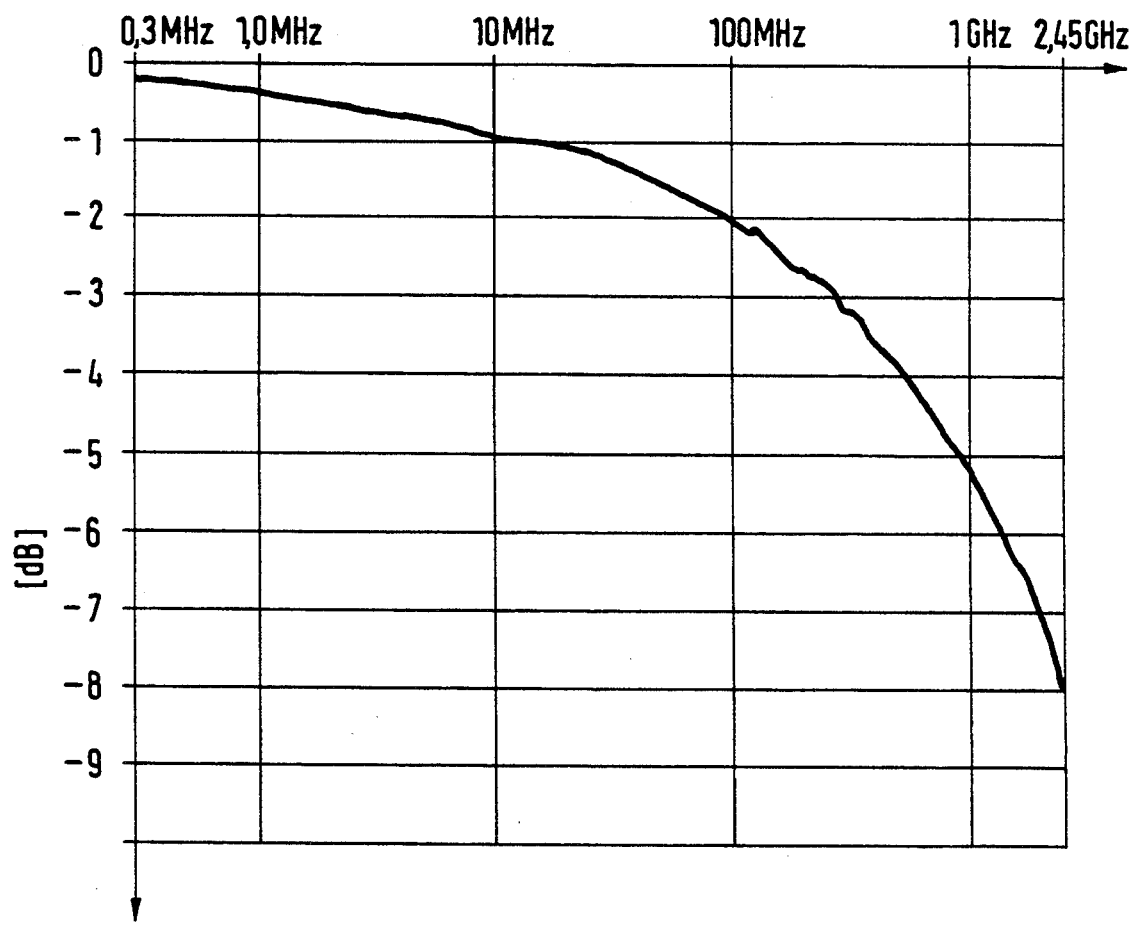
FIG. 3 is a diagram showing the cable attenuation of a conventional coaxial cable arrangement in relation to the high energy frequency.

The invention is best understood with reference to the accompanying drawings.

FIG. 1 shows the basic concept of an antenna arrangement as described in the present invention. A continuous inner conductor 1 extends from a proximal end 5, which may be designed in the form of a plug connector 4 by means of which the coaxial cable arrangement can be detachably connected with a high-frequency generator (not shown in the drawing) operating in the microwave range, to a distal end 6. In a first section A of the coaxial cable arrangement, which begins at the proximal end 5 and preferably measures between several decimeters to more than one meter in length, the coaxial cable arrangement is provided with an insulator 2 arranged cylindrically around the continuous inner conductor 1 and a continuous shielding device 3 applied over the insulator 2. The shielding device 3 consists of a thin metal wire or thin metallic flat conductors in either knitted, braided or wrapped form. In a second section B, the inner conductor lies exposed and, being an asymmetric rod dipole, serves as a transmitting antenna 8 for high-frequency energy in the microwave range. The second section B may measure several centimeters in length. In order to impart a certain minimum rigidity to the proximal area of the coaxial cable assembly, so that it can be inserted and pushed forward in a guiding lumen or a dilatation catheter, a third section C of the coaxial cable assembly, beginning at the proximal end 5 and always being shorter than the first section A, is provided.

This third section C of the coaxial cable assembly has been subjected to wave treatment in order to fill inherent gaps 30 in the knitted or wrapped shielding device 3 with a reinforcing, conductive mass 31, such as solder. The filling reinforcing conductive mass is, however, not restricted to the use of soldering material. All filling masses of sufficient electrical conductivity and reinforcement strength are suitable, including electrically conductive plastics such as semi-conductive polyfluoroamide (PFA) or dotted fluorothermoplastics such as FEP.

For applications where an increased flexibility of the coaxial cable arrangement is not needed at the distal end, for example, when the cable will not be used for hollow body organs, and where only the high-frequency characteristics are important, it may be preferable to fill the entire section A with a filling material.

The section between the distal end 7 of the third section C and the proximal end 10 of the second section B is not reinforced so that the coaxial cable arrangement within a dilatation catheter is easy to insert, for example, into the coronary arteries with their narrow bends without danger of injury.

In a preferred embodiment, the coaxial cable arrangement described in the present invention is provided with an insertion stop 9 at the proximal end 5 at a certain distance D from the distal end 6. This shows the user how far the coaxial cable arrangement has been inserted into the catheter (not shown in the drawing) and prevents any pushing beyond this maximum admissible point. It is preferable to cover the part of the coaxial cable arrangement from the proximal end 5 to the stop 9 with an insulating outer jacket 11 made of FEP, PFA, or PTFE. The stop may also be formed with the face of the jacket 11 which ends at the stop.

FIG. 2 shows another embodiment of an antenna arrangement with a metallic, electrically conductive antenna part 101, which is mounted to second section B of the coaxial cable arrangement in order to improve the high-frequency characteristics. The preferable shape is a cone with an obtuse base, which forms the outermost distal end 6 of the coaxial cable arrangement. The antenna part 101 allows for a more favorable adaptation of the wave impedance of the coaxial cable arrangement to the wave impedance of the tissue in the area of the catheter balloon. The remaining components of this embodiment are similar to those shown in FIG. 1. Whenever the components of FIGS. 1 and 2 are identical, the same reference numbers are used.

FIG. 3 is a diagram showing the cable attenuation of a conventional comparative coaxial cable measuring 3 m in length on the y-axis (marked off downwards) versus the high-frequency energy on the x-axis for frequencies ranging from 0.3 MHz to 2.5 GHz. In this embodiment the comparative coaxial cable resembles the coaxial cable arrangement used for the invention, the only difference being that inherent knitting, braiding or wrapping gaps in the shielding device 3 have not been filled by a conductive filling material.

Figure 4:
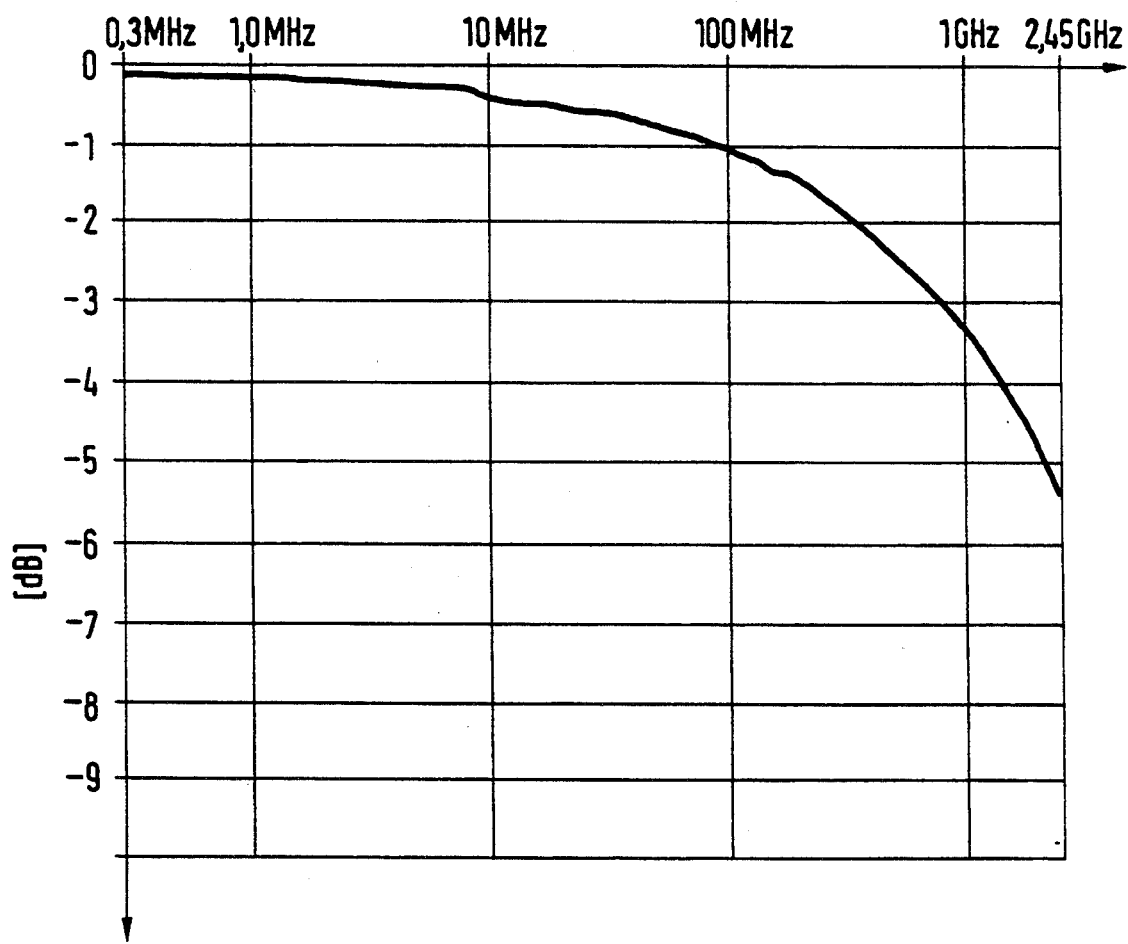
FIG. 4 is a diagram showing the attenuation of a coaxial cable assembly as described in the present invention in relation to the high energy frequency.

FIG. 4 is a diagram showing the cable attenuation of a 3 m long piece of the coaxial cable used for the arrangement described in the invention on the y-axis (marked off downwards) versus the high energy frequency ranging from 0.3 MHz to 2.5 GHz, wherein small gaps in the knitted or wrapped material of the shield 3 have been filled by solder in a wave bath.

A comparison of FIG. 3 to FIG. 4 reveals that the cable attenuation of the coaxial cable arrangement used rises considerably slower than for the comparative cable shown in FIG. 3. As apparent from the figures, the cable attenuation at a frequency of 2.45 GHz is approximately $-2.7$ dB/m for the comparative cable, whereas the cable constructed according to the invention has an attenuation of approximately $-1.83$ dB/m. This means that the undesired radiation of high-frequency energy outside of the antenna area 8 (101) itself is reduced by the filling of the little gaps so that the undesired heat dissipated due to the undesired high-frequency energy in the blood vessels, through which the catheter must be guided to reach the destination of the dilatation treatment, is reduced. This is a significant improvement of the state of the art, which may be utilized to shorten the duration of the dilatation treatment by increasing the high-frequency energy input supplied to the coaxial cable assembly. Despite the increased supply of energy, there is no danger that the blood vessels through which the catheter is guided will be damaged.

The present invention is not restricted to the above-mentioned treatment of the shielding device 3 with a filling material.

The coaxial cable arrangement must have the necessary mechanical properties, including increased rigidity or stiffness in the proximal area and a correspondingly lower rigidity or stiffness in the distal area also when different insulating materials of different rigidities are used for the insulator 2. Such a coaxial cable arrangement is provided with a third section C which begins at the proximal end 5 of the antenna arrangement and which is shorter than the first section A of the coaxial cable arrangement, wherein the insulator 2 in the third section C consists of a first insulating material. In the area between the distal end 7Z of the third section C and the proximal end 10 of the second section B, the insulator consists of a second insulating material 22. The mechanical rigidity of the first insulating material is higher than that of the second one. The first and the second insulating material have preferably the same dielectric constant to avoid any undesirable reflexion of high-frequency energy between the first and the second insulating material.

The antenna arrangement described in the invention is not restricted to use in blood vessels. It is also suitable for applications in other hollow body organs, such as the intestines and the vagina. A dielectric jacket, made from plastic, may be slipped over shielding device 3 continuously up to the proximal end 10 of the second section B, particularly in body cavities allowing a relatively large-sized catheter to be inserted. In this case, the rigidity of the coaxial cable arrangement may be changed in that a jacket material which is more rigid than the one used around the distal area is used as a sheath around the proximal area. T he advantage of this process is that reflected high-frequency energy cannot cause problems due to different dielectric constants of the insulator 2.

Since both the cable insulation and the jacket are best applied around the continuous inner conductor 1 or the shielding device 3 by an extrusion process, it is particularly simple and cost-saving to produce a coaxial cable arrangement with paired insulation materials or with paired sheathing materials in an extruder allowing the extrusion material to be changed, so that the first, more rigid insulation material or the first, more rigid sheathing material is used for the third section C while the insulation 2 or the insulating jacket 11 is extruded and the second, less rigid insulation material or the second, less rigid sheathing material is used for extruding the insulation 2 or the dielectric jacket 11 in the part of the first section A which does not belong to the third section C.

FIG. 5 is a schematic view of a dilatation catheter 110 with a coaxial cable arrangement 100 inserted therein and with an antenna arrangement mounted thereto. A high-frequency generator 114 produces high-frequency energy, of a frequency in the range of 2.45 GHz, which is supplied to the coaxial cable arrangement 100 through a plug-in connector 4a and 4b and which is radiated by means of the asymmetrical dipole formed by an antenna part 101 and the shielding device 3. The antenna part 101 is arranged in the distal end of a dilatation catheter 110 which is designed as a balloon 111. Apart from a first lumen 120, into which the coaxial cable arrangement 100 is inserted up to the stop 9, the catheter 110 comprises at least two other lumina 121, 122 as shown in FIG. 6. In a second lumen 121 a line 112 (shown in FIG. 5) is inserted through which a cooling liquid, for instance a salt solution can be guided through the catheter. By this means the undesired heat produced by the undesired high-frequency radiation of the coaxial cable arrangement 100 can be kept away from the wall of the vessel and taken away by the solution without harmful effects. A third lumen 113 contains a guiding wire 113. The sterile area of the dilatation catheter shown in the figure begins at the proximal end 5 of the coaxial cable arrangement 100 immediately after the plug connection 4 and extends up to the outermost distal end of the balloon 111. FIG. 6 is a cross-section A—A through the dilatation catheter 110 shown in FIG. 5, with a first lumen 120 for taking up the coaxial cable arrangement 100, with a second lumen 121 for taking up the cooling liquid and with a third lumen 122 for taking up the guiding wire 113. If only a small amount of cooling liquid is used, it can be given off to the blood circulation system through an outlet opening (not shown in the drawing). Other embodiments of the dilatation catheter 110 may provide for another lumen (not shown in the drawing) through which the cooling solution is fed back to the catheter inlet.

I CLAIM:

1. An antenna arrangement with a supply line in the form of a coaxial cable arrangement suitable for high frequencies, for medical applications requiring heat in hollow parts of a patient's body comprising:
   (a) a continuous inner conductor identified by three sections wherein a first section is a distal region relative to a user treating a patient and serves as a transmitting antenna, a second section is a proximal region relative to a user treating a patient, and a third section is an intermediate region located between the distal and proximal regions;
   (b) an insulator arranged cylindrically around the inner conductor covering the proximal and intermediate regions but does not extend to the distal region which serves as the transmitting antenna; and
   (c) a shielding device applied around the insulator which covers the proximal and intermediate regions, in which the shielding device is selected from the group consisting of knitted metal wire, wrapped metal wire and metal foil and further wherein the shielding device in the proximal region has gaps interspersed within the shielding device which are filled with a conductive reinforcing material which becomes rigid after application.

2. An antenna arrangement of claim 1, wherein the conductive reinforcing material is solder.

3. An antenna arrangement of claim 1, wherein the conductive reinforcing material is an electrically conductive plastic material.

4. An antenna arrangement of claim 1, wherein the coaxial cable arrangement is provided with an insertion stop arranged on the shielding device at a predetermined distance within the proximal region.

5. An antenna arrangement of claim 1, wherein the distal region is in the form of a cone so that obtuse cone base forms at the distal end of the coaxial cable arrangement.

6. An antenna arrangement with a supply line in the form of a coaxial cable arrangement suitable for high frequencies, for medical applications of heat in hollow parts of a patient's body, comprising:
   (a) a continuous inner conductor identified by three sections wherein a first section is a distal region relative to a user treating a patient and serves as a transmitting antenna, a second section is a proximal region relative to a user treating a patient, and a third section is an intermediate region located between the distal and proximal regions;
   a first insulator arranged cylindrically around the inner conductor of the proximal region and a second insulator arranged cylindrically around the inner conductor of the intermediate region wherein the first insulator has a mechanical rigidity greater than that of the second insulator; and (c) a shielding device applied around the insulators which covers the proximal and intermediate regions, in which the shielding device is selected from the group consisting of knitted metal wire, wrapped metal wire and metal foil.

7. An antenna arrangement of claim 6 wherein the insulator surrounding the proximal region has a dielectric constant equal to the dielectric constant of the insulator of the intermediate region.

8. An antenna arrangement as in claim 6 further comprising a first dielectric jacket surrounding the shielding in the proximal region and a second dielectric jacket surrounding the shielding device in the intermediate region, wherein the first insulator and first dielectric jacket comprise a thermoplastic material and wherein the second insulator and second dielectric jacket comprise a different thermoplastic insulating material.

9. An antenna arrangement as in claim 8 wherein the thermoplastic material of the first insulator and dielectric jacket are applied to the cable arrangement by extrusion and the thermoplastic material of the second insulator and dielectric jacket are also applied by extrusion.

10. An antenna arrangement with a supply line in the form of a coaxial cable arrangement suitable for high frequencies, for medical applications requiring heat in hollow parts of a patient's body comprising:

(a) a continuous inner conductor identified by three sections wherein a first section is a distal region relative to a user treating a patient and serves as a transmitting antenna, a second section is a proximal region relative to a user treating a patient, and a third section is an intermediate region located between the distal region and proximal region;

(b) an insulator arranged cylindrically around the inner conductor covering the proximal and intermediate regions but does not extend to the distal region serving as the transmitting antenna;

(c) a shielding device applied around the insulator which covers the proximal and intermediate regions, in which the shielding device is selected from the group consisting of knitted metal wire, wrapped metal wire and metal foil;

(d) a first dielectric jacket surrounding the shielding in the proximal region, and (e) a second dielectric jacket surrounding the shielding device in the intermediate region, wherein the mechanical rigidity of the dielectric of the proximal region is greater than that of the dielectric of the intermediate region.

11. A dilation catheter having at least one lumen and incorporates an antenna arrangement with a supply line in the form of a coaxial cable arrangement suitable for high frequencies, for medical applications requiring heat in hollow parts of a patient's body, said antenna arrangement comprising:

(a) a continuous inner conductor identified by three sections wherein a first section is a distal region relative to a user treating a patient and serves as a transmitting antenna, a second section is a proximal region relative to a user treating a patient, and a third section is an intermediate region located between the distal end and proximal regions;

(b) an insulator arranged cylindrically around the inner conductor covering the proximal and intermediate regions but not extending to the distal region which serves as the transmitting antenna;

(c) a shielding device applied around the insulator which covers the proximal and intermediate regions, in which the shielding device is selected from the group consisting of knitted metal wire, wrapped metal wire and metal foil and further wherein the shielding device in the proximal region has gaps interspersed within the shielding device which are filled with a conductive reinforcing material which becomes rigid after application.

12. A dilation catheter of claim 11 having two lumena wherein the antenna arrangement is inserted into one of the lumen and a second lumen is connected to a source dispensing cooling liquid.

13. A dilation catheter of claim 12 wherein the second lumen is connected to a source dispensing a salt solution.

* * * * *